(12) United States Patent
Holmqvist (10) Patent No.: US 8,845,592 B2
(45) Date of Patent: Sep. 30, 2014

(54) MEDICAMENT DELIVERY DEVICE (75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 550 days.

(21) Appl. No.: 13/139,299

(22) PCT Filed: Nov. 26, 2009

(86) PCT No.: PCT/EP2009/065909
§ 371 (c)(1),
(2), (4) Date: Aug. 12, 2011

(87) PCT Pub. No.: WO2010/066591
PCT Pub. Date: Jun. 17, 2010

(65) Prior Publication Data
US 2011/0306936 A1  Dec. 15, 2011

Related U.S. Application Data

(60) Provisional application No. 61/122,372, filed on Dec. 13, 2008.

(30) Foreign Application Priority Data

Dec. 12, 2008 (SE) ........................................ 0850131
Dec. 12, 2008 (SE) ........................................ 0850132

(51) Int. Cl.
*A61M 5/00*  (2006.01)
*A61M 5/315*  (2006.01)
*A61M 5/24*  (2006.01)
*A61M 5/20*  (2006.01)
*A61M 15/00*  (2006.01)
*A61M 5/48*  (2006.01)
*A61M 11/00*  (2006.01)

(52) U.S. Cl.
CPC ......... *A61M 5/20* (2013.01); *A61M 2005/2488* (2013.01); *A61M 5/31501* (2013.01); *A61M 2005/2407* (2013.01); *A61M 2005/2492* (2013.01); *A61M 2005/2073* (2013.01); *A61M 15/00* (2013.01); *A61M 5/24* (2013.01); *A61M 5/482* (2013.01); *A61M 11/00* (2013.01); *A61M 5/2033* (2013.01)
USPC ........... 604/187; 604/218; 604/225; 604/228; 604/229; 604/230

(58) Field of Classification Search
USPC ......... 604/181, 187, 199, 218, 225, 228, 229, 604/230
See application file for complete search history.

(56) References Cited

U.S. PATENT DOCUMENTS 5,092,842 A * 3/1992 Bechtold et al. .............. 604/135
5,320,609 A * 6/1994 Haber et al. ................... 604/135
5,480,387 A * 1/1996 Gabriel et al. ................ 604/134
6,641,566 B2  11/2003 Douglas et al.
2008/0071226 A1* 3/2008 Moser et al. .................. 604/207

FOREIGN PATENT DOCUMENTS

GB  662352 A  12/1951
GB  2443390 A  5/2008
WO  01/93926 A2  12/2011

OTHER PUBLICATIONS

EPO, Int'l Search Report in PCT/EP2009/065909, Apr. 20, 2010.
EPO, Written Opinion in PCT/EP2009/065909, Apr. 20, 2010.
EPO, Int'l Preliminary Report on Patentability in PCT/EP2009/065909, Jun. 14, 2011.

* cited by examiner

*Primary Examiner* — Emily Schmidt
*Assistant Examiner* — Lauren M Peng
(74) *Attorney, Agent, or Firm* — Piedmont Intellectual Property

(57) ABSTRACT

The present invention relates to a medicament delivery device (10) comprising a front housing (12) and a rear housing (14) connected to each other; a medicament container (18) disposed within the front housing (12), wherein the container (18) has a front opening with or for a delivery member for delivering the medicament therethrough and at least one movable stopper (25); and a compression spring (26) having a predetermined compressed length and a predetermined outer diameter, wherein the compressed length is the length of the spring when it is in a pre-tensioned state; wherein the device further comprises a first guide means comprising a front part (28) having a predetermined first length (61), a middle part (42) having a predetermined second length (62), and a rear part (34) having a predetermined third length (63), wherein said predetermined third length corresponds to the predetermined compressed length of the compression spring, wherein the front part (28) is arranged to be in contact with the movable stopper (25), wherein the middle part comprises an annular ledge (41) and first lock-release means (43), and wherein the rear part (34) is fully surrounded by the compression spring when it is in its pre-tensioned state; and a second guide means which constitutes a generally tubular inner wall (32) of the rear housing (14) having a predetermined fourth length (64), a rear end surface (31), a predetermined inner diameter, and second lock-release means, wherein the predetermined fourth length corresponds to the predetermined first (61) and the predetermined second (62) lengths together, and wherein the predetermined inner diameter of the second guide means is somewhat larger than the predetermined outer diameter of the compression spring, such that the compression spring is fully arranged inside said second guide means between the rear end surface (31) and the annular ledge (41) when it is in its pre-tensioned state.

14 Claims, 6 Drawing Sheets

MEDICAMENT DELIVERY DEVICE

TECHNICAL AREA

The present invention relates to a medicament delivery device and in particular a device intended to self-administration of medicament.

TECHNICAL BACKGROUND

Medicament delivery devices developed for self-administration have become very popular because they allow for the users to provide medicament without the need for visiting a hospital, a clinic or the like in order to receive an injection of medicament.

The devices for self-administration that have been developed contain different degrees of functionality depending e.g. on the application, type of drug and intended user. The different functions may include automatic penetration, injection, mixing, priming, withdrawal from injection site, needle shields, to mention a few.

The majority of injection devices on the market are arranged with elongated, generally tubular medicament containers having one end where an injection needle can be attached, and provided with a movable wall at the other end, such as a rubber stopper. It is further very common to have some sort of elongated driver acting on said stopper, such as a plunger rod. The driver is also often connected to a power source such as compression springs, clock springs, and the like for urging the plunger rod against the stopper for expelling medicament through the injection needle.

The use of plunger rods is very well developed and they may be moved forward by the power source either linearly or rotatingly. A general desire from many users is to have as small devices as possible in order that they shall not attract too much attention, especially when the devices sometimes are to be used in the public. A problem with the above mentioned use of plunger rods is that the device has to be at least somewhat longer than the length of the medicament container plus the length of the plunger rod. The length problem becomes even more pronounced when functionality is added to the injector, such as dose setting buttons, needle shields extending from the injector, to mention some components. The problem is also more pronounced the longer the plunger has to move inside the medicament container, either that the doses are large or that the injector is designed to deliver a number of doses before the container is emptied.

A few attempts have been made to solve this problem. One such solution is shown in document U.S. Pat. No. 6,641,566 where the power source is placed parallel to the medicament container. Here the plunger rod is designed flexibly bendable around a wheel in order that the power source can act on the container via the plunger rod. However, even if the device becomes shorter, by necessity it becomes thicker and also obtains a shape that is more difficult to hold for a user. This means that the device is not as discrete as desired. Further, many patients have by now gotten used to injectors having a general pen-shape and are thus reluctant to adapt to other shapes. Another examples are shown in WO0193926 A2 and GB 2 443 390 A.

There is thus room for improvement regarding the size and design of injector.

BRIEF DESCRIPTION OF THE INVENTION

The aim of the present invention is to remedy the drawbacks with the known solutions of medicament delivery devices. This aim is obtained by a medicament delivery device according to the features of the independent patent claim. Preferably embodiments of the invention form the subject of the dependent patent claims.

According to a main aspect of the present invention it is characterised by a medicament delivery device comprising a front housing and a rear housing connected to each other; medicament container disposed within the front housing, wherein the container has a front opening with or for a delivery member for delivering the medicament therethrough and at least one movable stopper; and a compression spring having a predetermined compressed length and a predetermined outer diameter, wherein the compressed length is the length of the spring when it is in a pre-tensioned state; wherein the device further comprises first guide means comprising a front part having a predetermined first length, a middle part having a predetermined second length, and a rear part having a predetermined third length, wherein said predetermined third length corresponds to the predetermined compressed length of the compression spring, wherein the front part is arranged to be in contact with the movable stopper, wherein the middle part comprises an annular ledge and first lock-release means, and wherein the rear part is fully surrounded by the compression spring when it is in its pre-tensioned state; and a second guide means which constitutes a generally tubular inner wall of the rear housing having a predetermined fourth length, a rear end surface, a predetermined inner diameter, and second lock-release means, wherein the predetermined fourth length corresponds to the predetermined first and the predetermined second lengths together, and wherein the predetermined inner diameter of the second guide means is somewhat larger than the predetermined outer diameter of the compression spring, such that the compression spring is fully arranged inside said second guide means between the rear end surface and the annular ledge when it is in its pre-tensioned state.

According to another aspect of the invention, the device further comprises an activation member operably connected to the second guide means.

According to a further aspect of the invention, activation member is arranged to be movable in a predetermined direction from a locked state in which said activation member forces the second lock-release means to engage to the first lock-release means, to a released state in which the activation member allows the second lock release means to disengage from the first lock-release means.

According to yet another aspect of the invention, the annular ledge is arranged adjacent an annular front end of the rear part, and the first lock-release means is an annular slot arranged between the annular ledge and an annular rear end of the front part.

According to yet a further aspect of the invention, the second lock-release means are a number of flexible tongues having inwardly ledges adapted to fit into the annular slot, wherein said flexible tongues are arranged at the front end of the second guide means.

According to another aspect of the invention, the activation member comprises an activation button arranged through a longitudinally recess on the rear housing, and a sleeve-shaped part coaxially and slidably arranged on the front end of the second guide means, wherein said activation member is arranged to be movable in the predetermined direction from its locked state in which said sleeve-shaped part surrounds the flexible tongues such that the inwardly ledges are engaged in the annular slot and thereby hold the compression spring in the pre-tensioned state, to its released state in which said sleeve-shaped part allows the flexible tongues to flex radially outward such that the inwardly ledges are disengaged from the annular slot and thereby the compression spring is released from its pre-tensioned state for exerting a force on said movable stopper.

According to a further aspect of the invention, the medicament container has a predetermined inner diameter that is somewhat larger than the predetermined outer diameter of the compression spring, such that when the compression spring is released from its pre-tensioned state, a front part of the compression spring is moved into the medicament container.

According to yet another aspect of the invention, the fourth length of the second guide means and the total length of the first guide means which total length corresponds to the length of the first length, of the second length and of the third length together, are such that the first guide means and the second guide means overlap each other for eliminating any buckling of the compression spring when the compression spring is released from its pre-tensioned state.

According to yet a further aspect of the invention, the device further comprises an activation lock means movable arranged on said rear housing adjacent the activation button and movable between a tamper proof position in which said activation button is locked for activating the device and an activation position in which said activation button is released for activating the device.

According to another aspect of the invention, the device further comprises control speed mechanism which comprises a longitudinal surface on each of the inwardly ledges of the tongues, arranged to co-act with the outer annular surface of the compression spring when the activation member is moved in an opposite direction.

There are a number of advantages with the present invention. According to the invention, the medicament delivery device is achieved having a shorter length and having a lesser outer diameter, which reduces the amount of material in the manufacturing and the number of components. The compression spring has a dual function in that it both acts as a drive means for performing a delivery of medicament and at the same time constitutes the actual means for pushing the stopper inside the medicament container in order to deliver medicament, i.e. acts as, or constitutes, a plunger rod. This is obtained in that the spring is guided on both its outside as well as inside. This eliminates the use of a conventional plunger rod for performing the pushing of the stopper with the aid of the spring. Also preferably the rear part of the first guide means and the front part of the second guide means are designed to overlap each other during the medicament delivery, thereby completely eliminating the risk of buckling. The activation member has also a dual function when co-acting with the second guide means, a first function is for holding and releasing the compression spring and a second function is for controlling the delivery speed when the compression spring is released from its pre-tensioned state.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

FIG. 1 shows an example of a medicament delivery device 10 according to the present invention, in the embodiment shown a medicament injector. It comprises a generally elongated housing consisting of two parts, a front housing 12 and a rear housing 14 that can be connected to each other in a suitable manner, for example releasibly, by threads 16, FIG. 2, bayonet fittings, snap-in connectors or the like, or fixedly by deep grooves, by gluing, welding or the like depending on the application and intended use.

Figure 3:
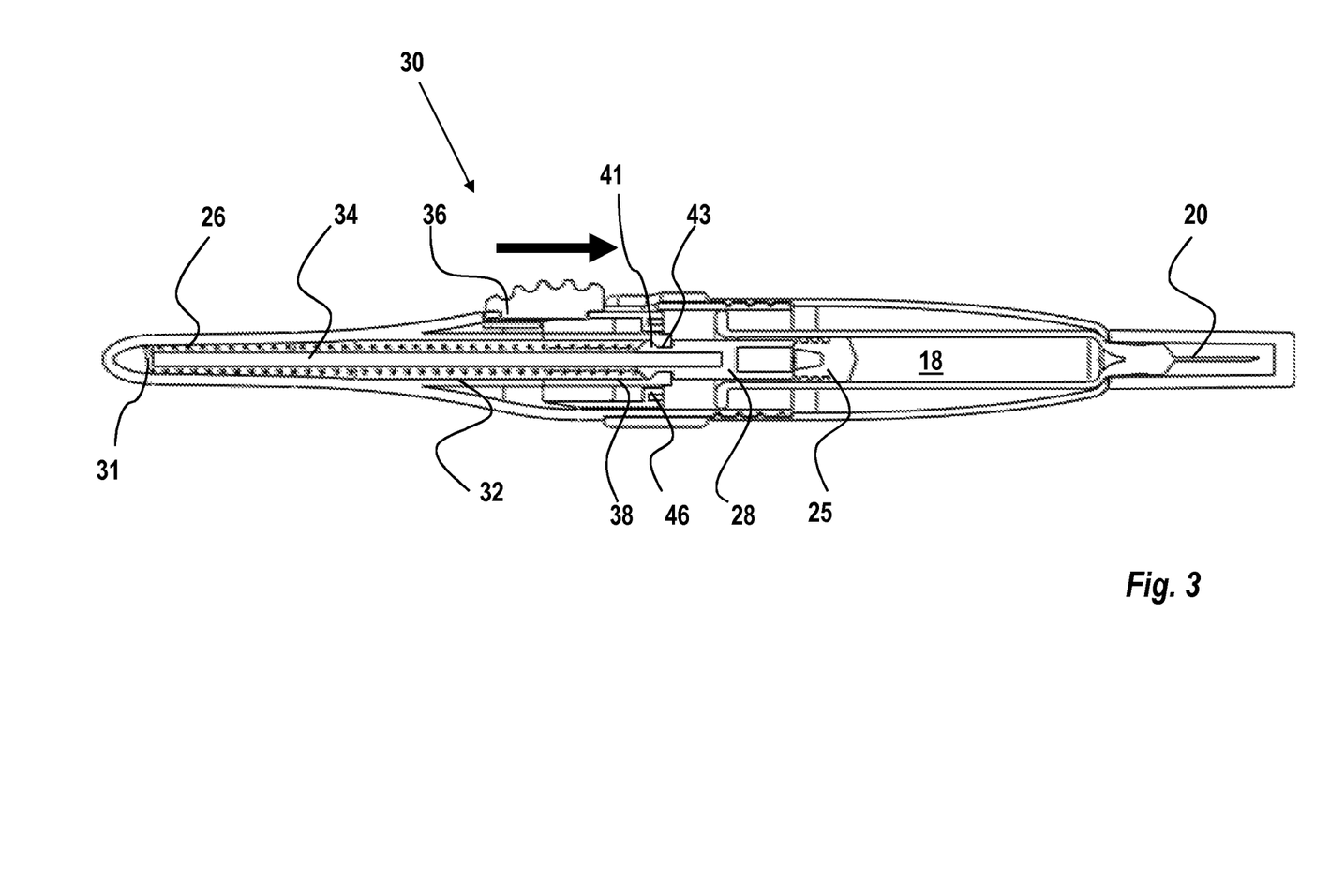
FIG. 3 is a side view on cross-section of the device of FIG. 1*a* when delivered to a user.

A medicament container 18 disposed within the front housing, wherein the container has a front opening with or for a delivery member for delivering the medicament therethrough and at least one movable stopper 25 FIG. 3. In the embodiment shown in the drawings, the medicament container 18 is a syringe with a needle 20 which protrudes though an opening in the front end of the front housing 12. When the device is in a pre-loaded state, the needle 20 is protected by a removable sheath 24.

The device also comprises a compression spring 26 having a predetermined compressed length and a predetermined outer diameter, wherein the compressed length is the length of the spring when it is in a pre-tensioned state. The compression spring in the shown embodiment of the figures is a coil spring having a predetermined number of windings which form an outer annular surface.

Figure 2:
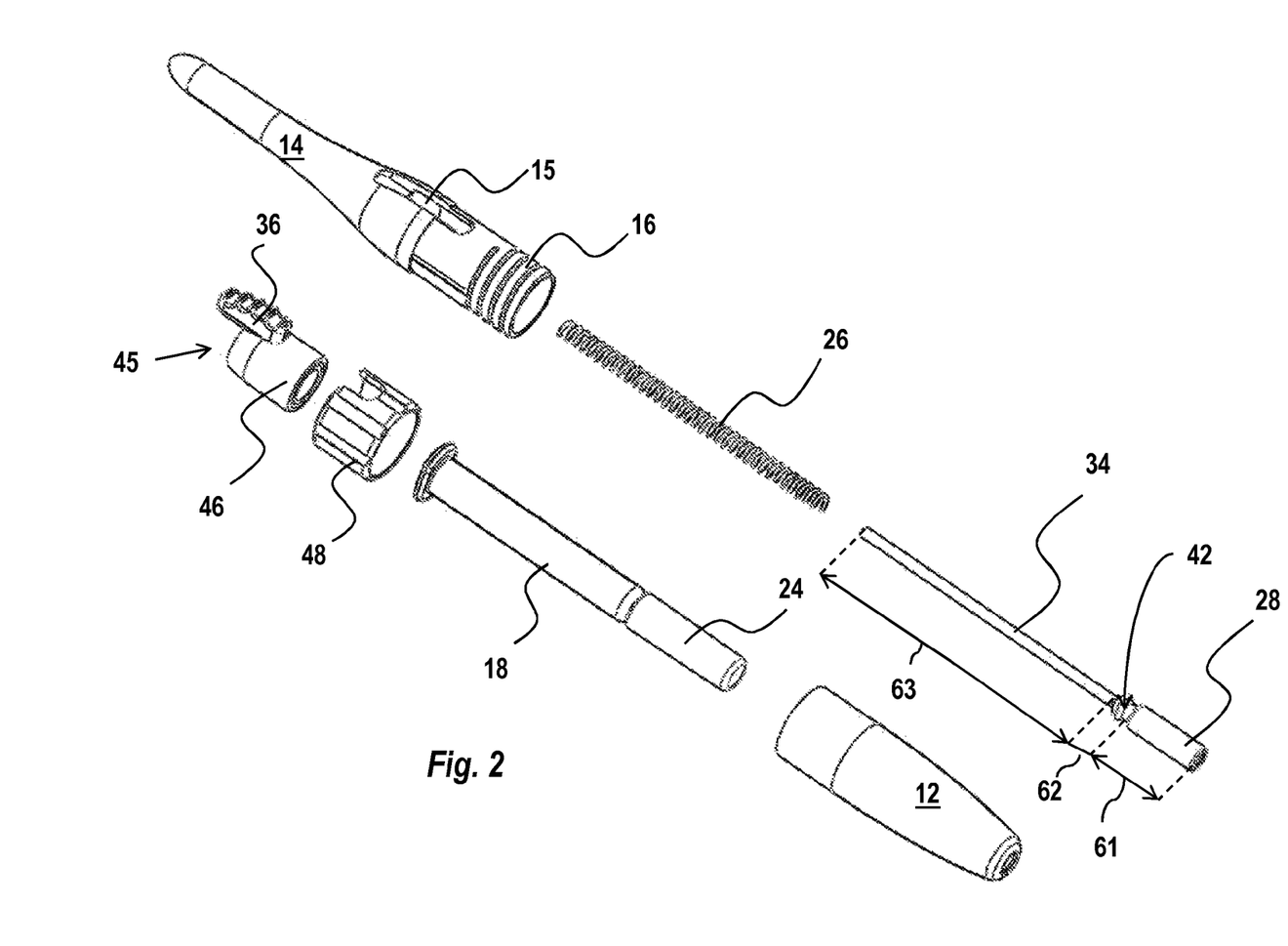
FIG. 2 is an exploded view of the device of FIG. 1*a*.
Figure 4:
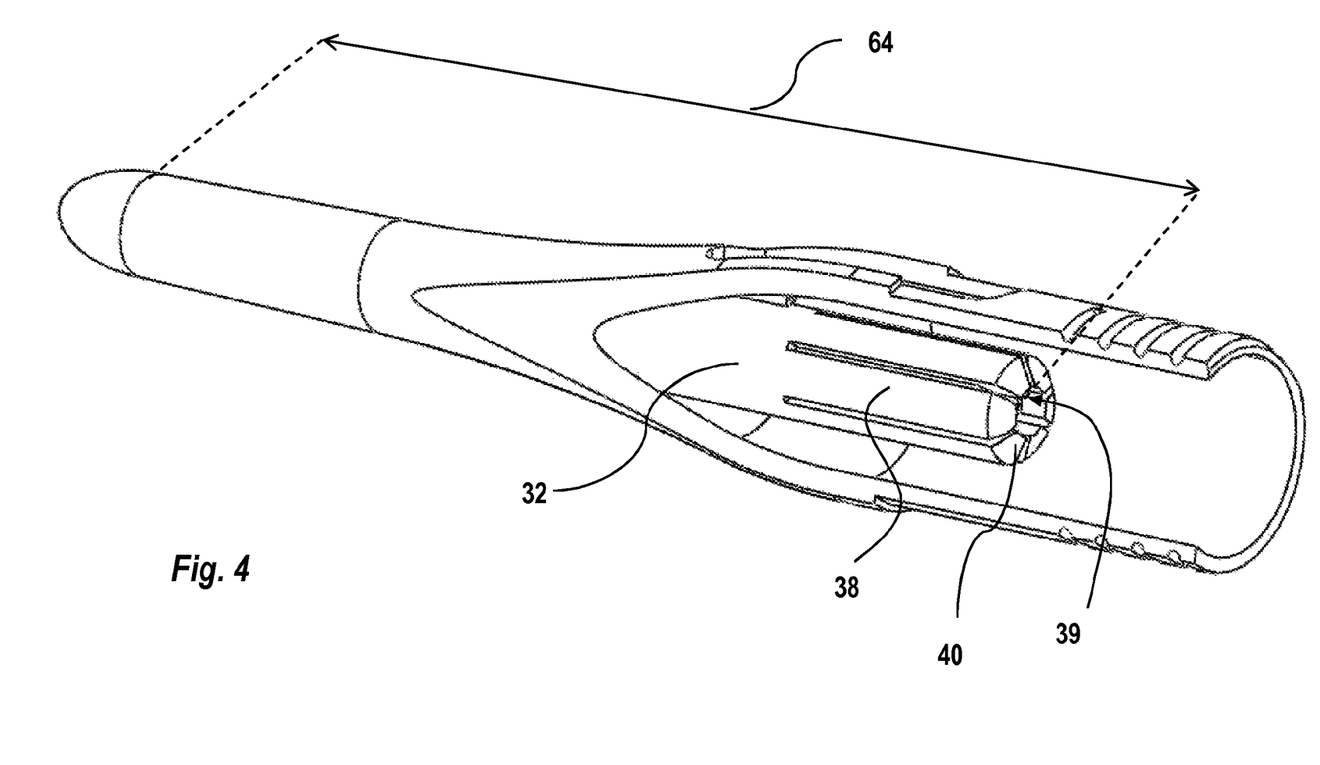
FIG. 4 is a detailed view partly in cross section of the rear housing of the device of FIG. 1*a*, and FIGS. 5-6 are side views in cross-section of different functional stages of the device of FIG. 1*a*.

The device further comprises a first guide means comprising a front part 28 having a predetermined first length 61, a middle part 42 having a predetermined second length 62, and a rear part 34 having a predetermined third length 63, FIG. 2, wherein said predetermined third length corresponds to the predetermined compressed length of the compression spring, wherein the front part 28 is arranged to be in contact with the movable stopper 25, wherein the middle part comprises an annular ledge 41 and first lock-release means 43, and wherein the rear part 34 is fully surrounded by the compression spring when it is in its pre-tensioned state, FIG. 3; and a second guide means which constitutes a generally tubular inner wall 32 of the rear housing 14 having a predetermined fourth length 64, a rear end surface 31, a predetermined inner diameter, and second lock-release means, FIG. 4, wherein the predetermined fourth length corresponds to the predetermined third 63 and the predetermined second 62 lengths together, and wherein the predetermined inner diameter of the second guide means is somewhat larger than the predetermined outer diameter of the compression spring, such that the compression spring is fully arranged inside said second guide means between the rear end surface 31 and the annular ledge 41 when it is in its pre-tensioned state, FIG. 3.

The device further comprises an activation member 45 operably connected to the second guide means, FIG. 2. The activation member 45 is arranged to be movable in a predetermined direction from a locked state in which said activation member forces the second lock-release means to engage to the first lock-release means, to a released state in which the activation member allows the second lock release means to disengage from the first lock-release means. The annular ledge 41 is arranged adjacent an annular front end of the rear part 34, and the first lock-release means is an annular slot 43 arranged between the annular ledge and an annular rear end of the front part 28, FIGS. 2 and 3. The second lock-release means are a number of flexible tongues 38 having inwardly ledges 40 adapted to fit into the annular slot 43, wherein said flexible tongues are arranged at the front end of the second guide means, FIG. 4. The flexible tongues 38 have a tendency to exert a radial outwardly force and form a passage 39, FIG. 4, through which the spring 26 can pass.

The activation member 45 comprises an activation button 36 arranged through a longitudinally recess 15 on the rear housing, and a sleeve-shaped part 46 coaxially and slidably arranged on the front end of the second guide means, FIG. 2. The sleeve-shaped part 46 comprises a passage with a diameter generally corresponding to the outer diameter of the tongues 38. The activation member 45 is arranged to be movable in a predetermined direction from its locked state in which said sleeve-shaped part surrounds the flexible tongues 38 such that the inwardly ledges 40 are engaged in the annular slot 43 and thereby hold the compression spring in the pre-tensioned state, to its released state in which said sleeve-shaped part allows the flexible tongues to flex radially outward such that the inwardly ledges 40 are disengaged from the annular slot and thereby the compression spring is released from its pre-tensioned state for exerting a force on said movable stopper.

The medicament container 18 has a predetermined inner diameter that is somewhat larger than the predetermined outer diameter of the compression spring 26, such that when the compression spring is released from its pre-tensioned state, a front part of the compression spring is moved into the medicament container.

The fourth length 64 of the second guide means and the total length of the first guide means which total length corresponds to the length of the first length 61, of the second length 62 and of the third length 63 together, are such that the first guide means and the second guide means overlap each other for eliminating any buckling of the compression spring when the compression spring 26 is released from its pre-tensioned state.

Figures 1A, 1B:
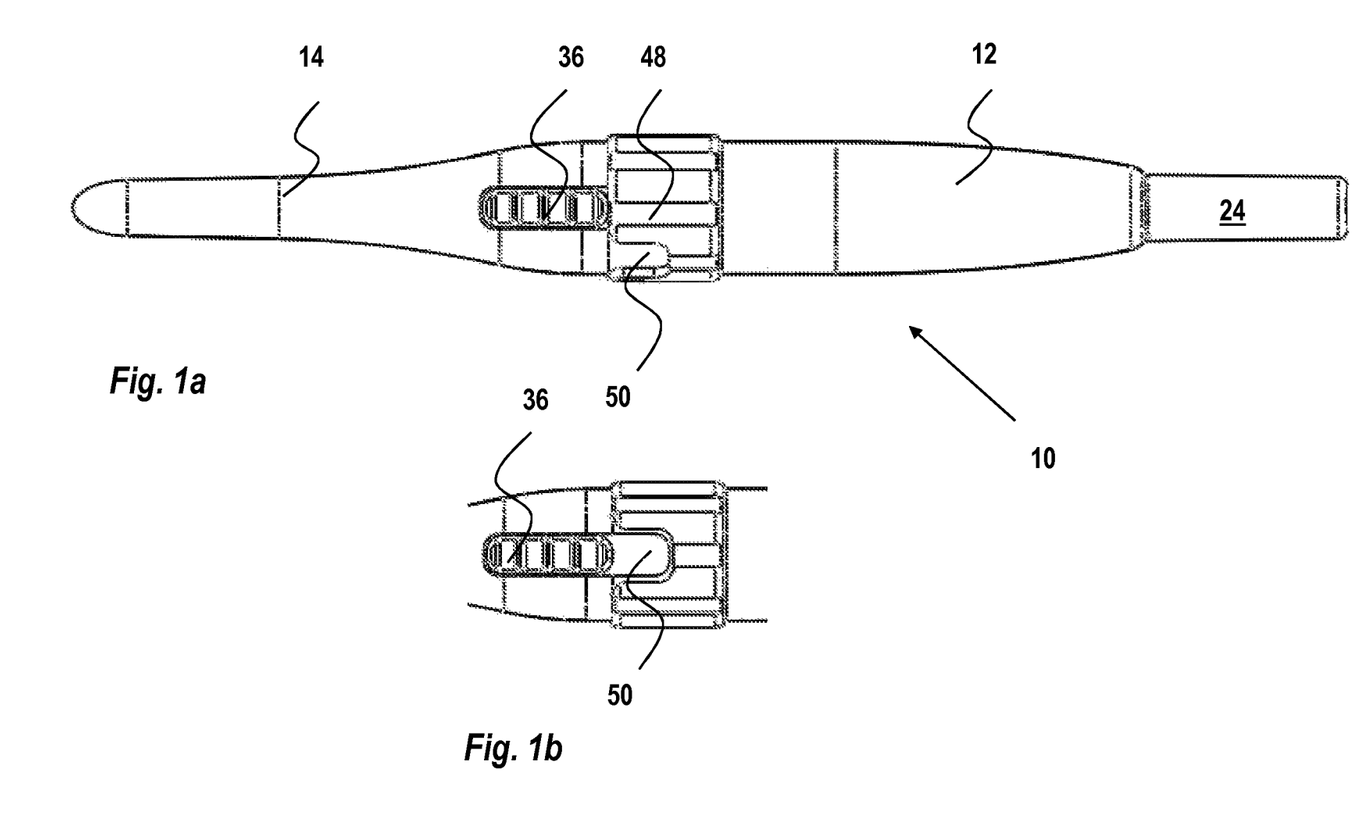
FIG. 1*a* is a side view of an embodiment of the present invention.
FIG. 1*b* is a detailed view taken from FIG. 1*a*.

The device further comprises an activation lock means 48 movable arranged on said rear housing adjacent the activation button 36 and movable between a tamper proof position in which said activation button 36 is locked for activating the device, FIG. 1a, and an activation position in which said activation button 36 is released for activating the device, FIG. 1b. In the embodiment shown the activation lock means 48 is a sleeve arranged rotatable on the rear housing adjacent the activation button 36. The activation lock means is arranged with a groove 50 in which the activation button fits when said activation means is turned from its tamper proof position to its activation position, FIG. 1b.

The device further comprises a control speed mechanism which comprises a longitudinal surface on each of the inwardly ledges 40 of the tongues 38, arranged to co-act with an outer annular surface of the compression spring when the activation member is moved in an opposite direction.

In the embodiment shown in FIG. 4, each of the inwardly ledges 40 of the tongues 38 comprises bevelled surfaces which are arranged to co-act with an annular bevelled surface on the inner annular surface of the sleeve-shaped part 46, such that when the activation member is moved in an opposite direction, the annular bevelled surface of said sleeve-shaped part is pressed against each of the bevelled surfaces on the inwardly ledges 40 of the tongues 38, whereby each longitudinal surface on each of the inwardly ledges 40 of the tongues 38, is pressed against the outer annular surface of the compression spring.

The device is intended to function as follows. The device could either be delivered completely assembled with the medicament container inside the housing, whereby the user merely has to attach a delivery member as e.g. needle 16, or remove a sheath before use; or the device may be delivered without the medicament container 18, either in two halves 12, 14 or temporarily assembled, whereby the user has to insert a medicament container 18, in the embodiment shown a syringe, into the front housing and assemble the two parts.

When the medicament is to be delivered, the device is activated by moving the activation lock means 48 from the tamper proof position to the activation position in which said activation button 36 is released for activating the device. The device of the example is then placed at the delivery site and when the device is an injector, the needle 20 penetrates the skin.

Figure 5:
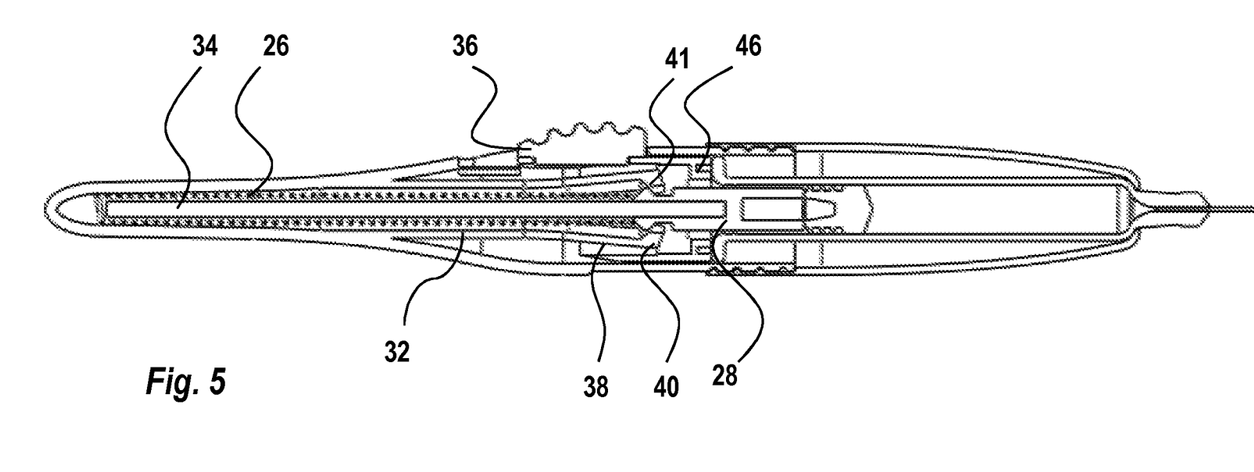
Figure 6:
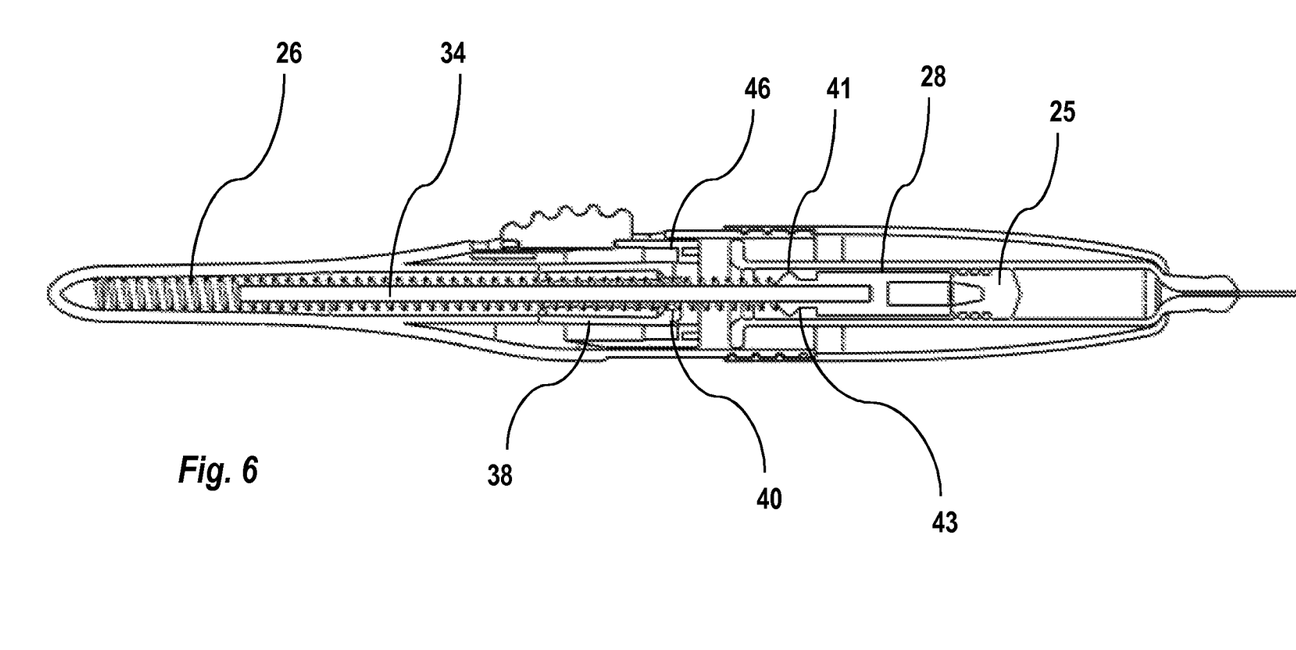

When the compression spring is to be released from its pre-tensioned state, the user then slides the activation button 36 towards the front end of the device, to the right in the direction of the arrow of FIG. 3. This movement causes the sleeve-shaped part 46 of the lock-release means to move in the same direction, whereby it is moved out of contact with the tongues 38, which in turn causes the ledges 40 to move out of contact with the annular slot 43, FIG. 5. The first guide means is thus free to move forward due to the force of the pre-tensioned compression spring 26 acting on the annular protrusion 41 whereby the stopper 25 is also moved forward inside the medicament container 18 to deliver the medicament through the delivery member e.g. a needle, FIG. 6. Due to the predetermined inner diameter of the tubular inner wall 32 of the rear housing 14 which is only somewhat larger than the predetermined outer diameter of the compression spring 26, due to the predetermined outer diameter of the compression spring which is only somewhat lesser than the inner diameter of the medicament container, due to the fourth length 64 of the second guide means, and due to the total length of the first guide means; the compression spring 26 is prevented from buckling when the compression spring 26 is released from its pre-tensioned state. As seen in FIG. 6, the tubular inner wall 32 of the rear housing 14 surrounds the rear part of the compression spring, the inner wall of the medicament container surrounds the front part of the compression spring, and the rear part 34 of the first guide means surrounded by the compression spring overlaps with the tubular inner wall 32 of the rear housing 14 for eliminating any buckling of the compression spring when the compression spring 26 is released from its pre-tensioned state and moves within said medicament container 18.

However, should the user during the medicament delivery feel that he/she needs to temporarily stop the medicament delivery due to e.g. pain because of the injected medicament, and/or wishes to slow down the medicament delivery speed; the activation button 36 is moved in the opposite direction. The movement of the button also causes the sleeve-shaped part 46 to move in the same direction whereby its bevelled annular surface comes in contact with the bevelled surfaces on the inwardly ledges 40 of the tongues 38. Due to the bevelled surfaces interacting with each other, the tongues, and thereby the longitudinal surfaces of the inwardly directed ledges 40 are pressed against the outer annular surface compression spring 26. This causes the compression spring to move slower the more the activation button is pressed and even to stop the movement of the compression spring completely. The longitudinal length of each longitudinal surface of the inwardly ledges 40 is preferably chosen such that there is no risk that the inwardly ledges 40 will be caught between the windings of the spring.

The wording medicament container may embrace several different types of containers such as cartridges, ampoules, syringes, vials, aerosol containers, just to mention a few. In that respect the present invention could also be used with other types of medicament delivery devices such as powder or aerosol inhalers as well as nebulizers, wherein the delivery member is a mouth piece or nasal piece or a nozzle and capable of delivering a dose of medicament to be inhaled by the patient.

It is to be understood that the embodiment described above and shown in the drawings is to be regarded only as a non-limiting example of the present invention and that it may be amended in many ways within the scope of the patent claims.

The invention claimed is:

1. A medicament delivery device, comprising:
a front housing and a rear housing connected to each other;
a medicament container disposed within the front housing and having a front opening for a delivery member for delivering medicament therethrough and at least one movable stopper;
a compression spring having a predetermined compressed length and a predetermined outer diameter, wherein the compressed length is the length of the spring when the spring is in a pre-tensioned state;
a first guide mechanism, comprising a front part having a predetermined first length, a middle part having a predetermined second length, and a rear part having a predetermined third length that corresponds to the predetermined compressed length of the compression spring, wherein the first part extends from a front tip of the first guide mechanism to a front end of the middle part, the middle part extends from a rear end of the front part to a front end of the rear part, the rear part extends from a rear part of the middle part to a rear tip of the guide mechanism, the front tip of the front part is arranged to be in contact with the movable stopper, the middle part comprises an annular ledge and a first lock-release device, and the rear part is fully surrounded by the compression spring when the spring is in the pre-tensioned state such that the spring in the pre-tensioned state extends from the rear tip of the rear part to the rear end of the middle part; and
a second guide mechanism, comprising a generally tubular inner wall of the rear housing having a predetermined fourth length, a rear end surface, a predetermined inner diameter, and a second lock-release device, wherein the predetermined fourth length corresponds to the predetermined third length and the predetermined second length together, and the predetermined inner diameter is larger than the predetermined outer diameter of the compression spring, such that the compression spring is fully arranged inside the second guide mechanism between the rear end surface and the annular ledge when the spring is in the pre-tensioned state.

2. The medicament delivery device of claim 1, further comprising an activation member operably connected to the second guide mechanism.

3. The medicament delivery device of claim 2, wherein the activation member is movable in a predetermined direction from a locked state, in which the activation member forces the second lock-release device to engage the first lock-release device, to a released state, in which the activation member allows the second lock-release device to disengage from the first lock-release device.

4. The medicament delivery device of claim 3, wherein the annular ledge is adjacent an annular front end of the rear part, and the first lock-release device includes an annular slot arranged between the annular ledge and an annular rear end of the front part.

5. The medicament delivery device of claim 4, wherein the second lock-release device includes a number of flexible tongues having inward ledges adapted to fit into the annular slot, and the flexible tongues are arranged at a front end of the second guide mechanism.

6. The medicament delivery device of claim 5, further comprising a control speed mechanism that includes a longitudinal surface on each of the inward ledges of the tongues, arranged to co-act with the outer annular surface of the compression spring when the activation member is moved in an opposite direction.

7. The medicament delivery device of claim 5, wherein the activation member comprises an activation button arranged through a longitudinal recess on the rear housing, and a sleeve-shaped part coaxially and slidably arranged on the front end of the second guide mechanism, and the activation member is arranged to be movable in the predetermined direction from the locked state, in which the sleeve-shaped part surrounds the flexible tongues such that the inward ledges are engaged in the annular slot and thereby hold the compression spring in the pre-tensioned state, to the released state, in which the sleeve-shaped part allows the flexible tongues to flex radially outward such that the inward ledges are disengaged from the annular slot and thereby the compression spring is released from the pre-tensioned state for exerting a force on the movable stopper.

8. The medicament delivery device of claim 7, further comprising a control speed mechanism that includes a longitudinal surface on each of the inward ledges of the tongues, arranged to co-act with the outer annular surface of the compression spring when the activation member is moved in an opposite direction.

9. The medicament delivery device of claim 7, wherein the medicament container has a predetermined inner diameter that is larger than the predetermined outer diameter of the compression spring such that when the compression spring is released from the pre-tensioned state, a front part of the compression spring is moved into the medicament container.

10. The medicament delivery device of claim 9, further comprising a control speed mechanism that includes a longitudinal surface on each of the inward ledges of the tongues, arranged to co-act with the outer annular surface of the compression spring when the activation member is moved in an opposite direction.

11. The medicament delivery device of claim 9, wherein the fourth length of the second guide mechanism and a total length of the first guide mechanism that corresponds to the first, second, and third lengths together are such that the first guide mechanism and the second guide mechanism overlap for reducing buckling of the compression spring when the compression spring is released from the pre-tensioned state.

12. The medicament delivery device of claim 11, further comprising a control speed mechanism that includes a longitudinal surface on each of the inward ledges of the tongues, arranged to co-act with the outer annular surface of the compression spring when the activation member is moved in an opposite direction.

13. The medicament delivery device of claim 11, further comprising an activation lock device arranged on the rear housing adjacent the activation button and movable between a tamper-proof position, in which the activation button is locked for activating the device, and an activation position, in which the activation button is released for activating the device.

14. The medicament delivery device of claim 13, further comprising a control speed mechanism that includes a longitudinal surface on each of the inward ledges of the tongues, arranged to co-act with the outer annular surface of the compression spring when the activation member is moved in an opposite direction.

* * * * *